United States Patent
Broz et al.

(10) Patent No.: US 10,210,283 B2
(45) Date of Patent: Feb. 19, 2019

(54) ACCESSIBILITY DETECTION AND RESOLUTION

(71) Applicant: INTERNATIONAL BUSINESS MACHINES CORPORATION, Armonk, NY (US)

(72) Inventors: Michal Broz, Austin, TX (US); Steven D. Clay, Round Rock, TX (US); John C. Sanchez, Pflugerville, TX (US); Richard S. Schwerdtfeger, Round Rock, TX (US); Lisa Seeman, Beit Shemesh (IL); Shunguo Yan, Austin, TX (US)

(73) Assignee: International Business Machines Corporation, Armonk, NY (US)

(*) Notice: Subject to any disclaimer, the term of this patent is extended or adjusted under 35 U.S.C. 154(b) by 110 days.

(21) Appl. No.: 15/278,342

(22) Filed: Sep. 28, 2016

(65) Prior Publication Data

US 2018/0089211 A1    Mar. 29, 2018

(51) Int. Cl.
*G06F 17/00* (2006.01)
*G06F 17/30* (2006.01)
(Continued)

(52) U.S. Cl.
CPC .......... *G06F 17/3097* (2013.01); *A61B 5/168* (2013.01); *A61B 5/4088* (2013.01); *G06F 17/30997* (2013.01)

(58) Field of Classification Search
CPC .. G06F 21/316; G06F 21/32; G06F 17/30867; G06F 21/31; G06F 17/30528; G06F 17/30864
See application file for complete search history.

(56) References Cited

U.S. PATENT DOCUMENTS

| 8,103,555 B2 | 1/2012 | Lee et al. |
| 8,166,135 B2 | 4/2012 | Ganesh et al. |

(Continued)

OTHER PUBLICATIONS

IBM, "Commerce Retail Solutions," IBM Commerce, p. 1-3, https://www.ibm.com/commerce/us-en/industries/retail/?ink=header-menu, Accessed on Sep. 26, 2016.
(Continued)

*Primary Examiner* — Truong V Vo
(74) *Attorney, Agent, or Firm* — Erik K. Johnson; Reza Sarbakhsh (57) ABSTRACT

A method for generating and presenting accessibility resolution models to accessibility problems is provided. The method may include detecting user behavior patterns associated with users. The method may further include generating user groups and subgroups based on the detected user behavior patterns. Additionally, the method may include identifying accessibility problems based on the detected user behavior patterns and the generated user groups and subgroups. The method may also include generating accessibility profiles based on the detected user behavior patterns, the generated user groups and subgroups, and the identified accessibility problems. The method may further include determining correlations between the generated accessibility profiles and business loss indicators. The method may also include generating and presenting accessibility resolution models to the identified accessibility problems based on the detected user behavior patterns, the generated user groups and subgroups, and the determined correlations between the generated accessibility profiles and business loss indicators.

20 Claims, 6 Drawing Sheets

(51) Int. Cl.
*A61B 5/00* (2006.01)
*A61B 5/16* (2006.01)

(56) References Cited

U.S. PATENT DOCUMENTS

| | | |
|---|---|---|
| 8,185,608 B1 | 5/2012 | York et al. |
| 8,312,097 B1 | 11/2012 | Siegel et al. |
| 8,606,725 B1 | 12/2013 | Agichtein et al. |
| 8,671,089 B2 | 3/2014 | Yu et al. |
| 8,843,484 B2 | 9/2014 | Gu et al. |
| 9,100,722 B2 | 8/2015 | Andrade |
| 9,646,322 B2 | 5/2017 | Minnis et al. |
| 2004/0095383 A1 | 5/2004 | Pfeifer et al. |
| 2010/0076274 A1 | 3/2010 | Severson |
| 2012/0254405 A1 | 10/2012 | Ganesh et al. |
| 2012/0284080 A1 | 11/2012 | De Oliveira et al. |
| 2014/0201038 A1 | 7/2014 | Minnis et al. |
| 2016/0044119 A1 | 2/2016 | Wirth et al. |
| 2016/0071143 A1 | 3/2016 | Pokorney et al. |
| 2016/0162912 A1 | 6/2016 | Garel et al. |
| 2016/0379267 A1 | 12/2016 | Cecchi et al. |
| 2017/0032274 A1 | 2/2017 | Yu et al. |
| 2017/0093996 A1 | 3/2017 | Amalapurapu et al. |

OTHER PUBLICATIONS

Kong et al., "Improving Passage Ranking with User Behavior Information," CIKM'13, Oct. 27-Nov. 1, 2013, p. 1999-2008, ACM, San Francisco, CA, USA.

Mell et al., "The NIST Definition of Cloud Computing," National Institute of Standards and Technology, Sep. 2011, p. 1-3, Special Publication 800-145.

Ramachandran et al., "Using Learned Application Flow to Predict Outcomes and Identify Trouble Spots in Network Business Transactions," Application and Drawings, Filed on Jul. 28, 2016, p. 1-38, U.S. Appl. No. 15/222,831.

Ramachandran et al., "Using Learned Application Flow to Assist Users in Network Business Transaction Based Apps," Application and Drawings, Filed on Jul. 28, 2016, p. 1-39, U.S. Appl. No. 15/222,850.

Takács et al., "Customer Habit Analysis in an e-commerce System Using Soft Computing Based Methods," IEEE International Conference on Fuzzy Systems (FUZZ-IEEE), Aug. 2-5, 2015, 6 Pages.

IBM: List of IBM Patents or Patent Applications Treated As Related (Appendix P), Nov. 15, 2017, pp. 1-2.

Broz et al., U.S. Appl. No. 15/813,185, filed Nov. 15, 2017, titled "Accessibility Detection and Resolution,", pp. 1-34.

ACCESSIBILITY DETECTION AND RESOLUTION

BACKGROUND

The present invention relates generally to the field of computing, and more specifically, to accessibility associated with user interfaces and computer devices.

Generally, one of the primary ways that users browse, complete tasks, and purchase goods and/or services is by using computer devices to access different applications. For example, online shopping is a form of electronic commerce (e-commerce) that allows consumers to directly buy goods or services from a provider using web browsers and online applications. Specifically, users may find products and services of interest by using a computer device to access programs, such as retailer websites or shopping apps, which allow users to interact with a user interface to browse the website and/or application and purchase products and services of interest. Therefore, usability factors such as ease of use and the presence of user-friendly features associated with computer devices and user interfaces may be considered for determining whether users use and return to a website or application, purchase goods or services from the websites/applications, and/or use particular computer devices to access the websites/applications. As such, usability testing is typically employed for finding problems and improvements to devices and applications.

SUMMARY

A method for generating and presenting a plurality of accessibility resolution models based on a plurality of user behavior patterns is provided. The method may include detecting the plurality of user behavior patterns associated with one or more users. The method may further include generating a plurality of user groups and a plurality of user subgroups based on the one or more users and the plurality of user behavior patterns. Additionally, the method may include identifying a plurality of accessibility problems based on the detected plurality of user behavior patterns, the generated plurality of user groups, and the generated plurality of user subgroups. The method may also include generating a plurality of accessibility profiles based on the detected plurality of user behavior patterns, the generated plurality of user groups, the generated plurality of user subgroups, and the identified plurality of accessibility problems. The method may further include determining at least one correlation between the generated plurality of accessibility profiles and at least one business loss indicator. The method may also include generating and presenting the plurality of accessibility resolution models for the identified plurality of accessibility problems based on the detected plurality of user behavior patterns, the generated plurality of user groups, the generated plurality of user subgroups, and the determined at least one correlation between the generated plurality of accessibility profiles and the at least one business loss indicator.

A computer system for generating and presenting a plurality of accessibility resolution models based on a plurality of user behavior patterns is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include detecting the plurality of user behavior patterns associated with one or more users. The method may further include generating a plurality of user groups and a plurality of user subgroups based on the one or more users and the plurality of user behavior patterns. Additionally, the method may include identifying a plurality of accessibility problems based on the detected plurality of user behavior patterns, the generated plurality of user groups, and the generated plurality of user subgroups. The method may also include generating a plurality of accessibility profiles based on the detected plurality of user behavior patterns, the generated plurality of user groups, the generated plurality of user subgroups, and the identified plurality of accessibility problems. The method may further include determining at least one correlation between the generated plurality of accessibility profiles and at least one business loss indicator. The method may also include generating and presenting the plurality of accessibility resolution models for the identified plurality of accessibility problems based on the detected plurality of user behavior patterns, the generated plurality of user groups, the generated plurality of user subgroups, and the determined at least one correlation between the generated plurality of accessibility profiles and the at least one business loss indicator.

A computer program product for generating and presenting a plurality of accessibility resolution models based on a plurality of user behavior patterns is provided. The computer program product may include one or more computer-readable storage devices and program instructions stored on at least one of the one or more tangible storage devices, the program instructions executable by a processor. The computer program product may include program instructions to detect the plurality of user behavior patterns associated with one or more users. The computer program product may further include program instructions to generate a plurality of user groups and a plurality of user subgroups based on the one or more users and the plurality of user behavior patterns. Additionally, the computer program product may also include program instructions to identify a plurality of accessibility problems based on the detected plurality of user behavior patterns, the generated plurality of user groups, and the generated plurality of user subgroups. The computer program product may further include program instructions to generate a plurality of accessibility profiles based on the detected plurality of user behavior patterns, the generated plurality of user groups, the generated plurality of user subgroups, and the identified plurality of accessibility problems. The computer program product may also include program instructions to determine at least one correlation between the generated plurality of accessibility profiles and at least one business loss indicator. The computer program product may also include program instructions to generate and present the plurality of accessibility resolution models for the identified plurality of accessibility problems based on the detected plurality of user behavior patterns, the generated plurality of user groups, the generated plurality of user subgroups, and the determined at least one correlation between the generated plurality of accessibility profiles and the at least one business loss indicator.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate generally to the field of computing, and more particularly, to accessibility associated with user interfaces and computer devices. The following described exemplary embodiments provide a system, method and program product for generating and presenting accessibility resolution models to accessibility problems associated with applications and devices. Therefore, the present embodiment has the capacity to improve the technical field associated with the accessibility of applications and devices by providing accessibility resolutions to accessibility problems based on user behavior patterns. Specifically, the present embodiment may provide accessibility resolution models by detecting user behavior patterns, and generating and presenting the accessibility resolution models based on correlations between the detected user behavior patterns, user groups and subgroups, cognitive impairments and disabilities, accessibility problems, and business loss indicators.

As previously described with respect to usability and accessibility associated with computer devices and user interfaces, usability factors such as ease of use and user-friendly features may be considered to determine whether users use certain computer devices, return to websites and applications, and purchase goods or services from websites/applications. Thus, usability testing is typically employed for finding problems and improvements to computer devices and user interfaces. However, current usability testing techniques do not account for cognitive disabilities and impairments associated with users. Specifically, businesses often attempt to adopt device and application designs without understanding how the designs may be experienced by different users/costumers who may suffer from disabilities and impairments, thereby producing devices and websites/applications that do not satisfy the different user expectations and needs which are not the same for all users.

Therefore, additional factors such as disabilities and impairments, culture, and increase in age may need to be considered when analyzing usability, as well as how such additional factors may correlate with loss of business and sales. For example, accessibility issues associated with user interfaces of online shopping websites and applications may occur due to disabilities and impairments associated with senior citizen consumers, whereby the disabilities and impairments are not recognized and/or not accounted for by the online shopping user interfaces. Therefore, the accessibility issues may lead to senior citizen customers abandoning online shopping transactions, which in turn may lead to decreased sales for businesses. As such, it may be advantageous, among other things, to provide a system, method and program product for determining accessibility deficiencies associated with computer devices and user interfaces by detecting user behavior patterns, and generating and presenting accessibility resolution models based on the detected user behavior patterns. Specifically, the system, method, and program product may detect user behavior patterns associated with applications and devices, identify device and application problems based on the detected user behavior patterns, and provide accessibility resolution models based on correlations between the detected user behavior patterns and business loss indicators.

According to at least one implementation of the present embodiment, user behavior patterns that are associated with user interfaces and computer devices may be detected. Furthermore, based on the detected user behavior patterns, user groups and user subgroups may be generated. Next, accessibility problems associated with the applications and devices may be identified based on the detected user behavior patterns and generated user groups and user subgroups. Then, cognitive accessibility profiles may be generated based on the detected user behavior patterns, the generated user groups and subgroups, and the identified accessibility problems. Next, correlations between the generated cognitive accessibility profiles and business loss indicators may be determined. Then, based on the determined correlations between the generated cognitive accessibility profiles and the business loss indicators, accessibility resolution models may be generated and presented.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD- ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product for generating and presenting accessibility resolution models based on user behavior patterns.

According to at least one implementation, user behavior patterns that are associated with user interfaces and computer devices may be detected. Furthermore, based on the detected user behavior patterns, user groups and user subgroups may be generated. Next, accessibility problems associated with the applications and devices may be identified based on the detected user behavior patterns and generated user groups and user subgroups. Then, cognitive accessibility profiles may be generated based on the detected user behavior patterns, the generated user groups and subgroups, and the identified accessibility problems. Next, correlations between the generated cognitive accessibility profiles and business loss indicators may be determined. Then, based on the determined correlations between the generated cognitive accessibility profiles and the business loss indicators, accessibility resolution models may be generated and presented.

Figure 1:
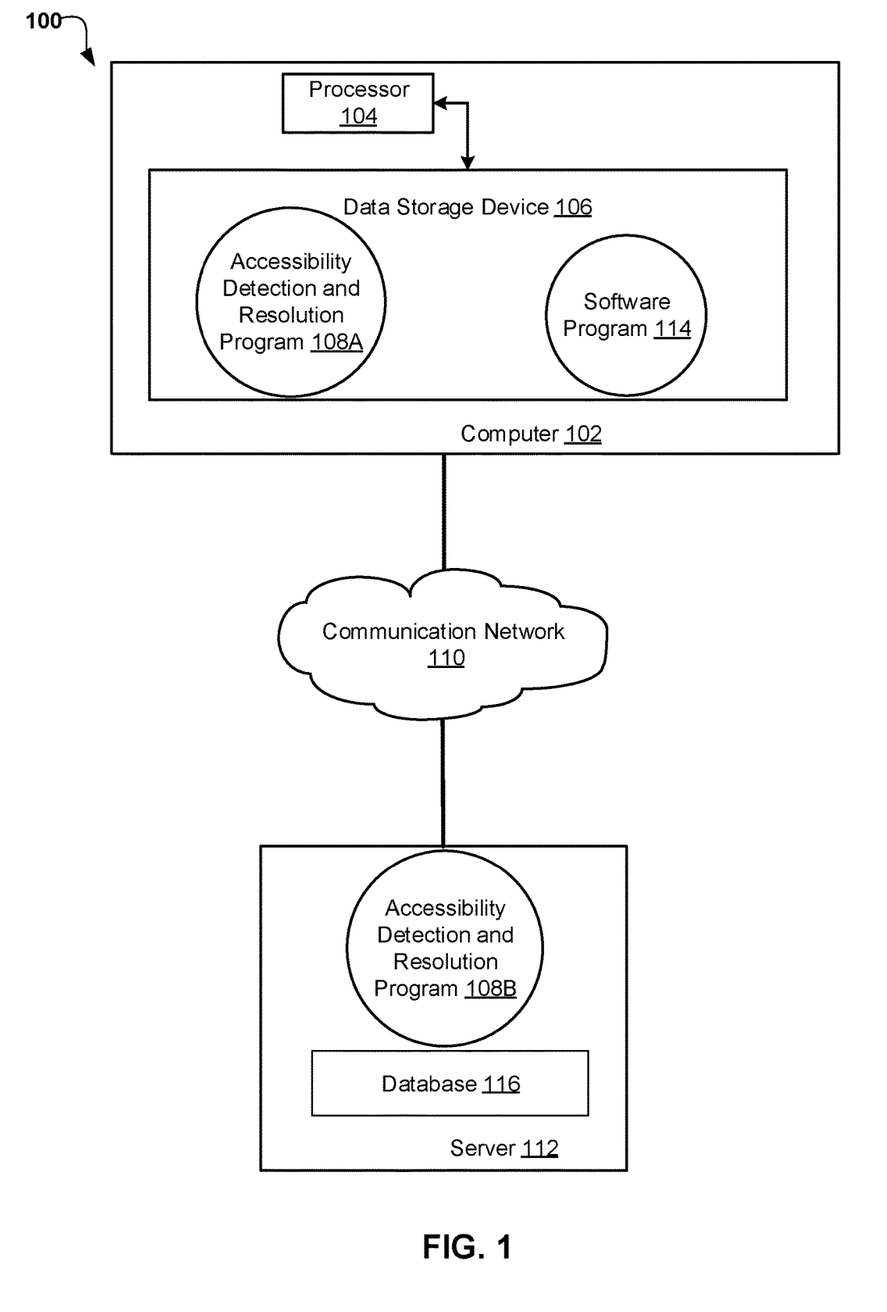
FIG. 1 illustrates a networked computer environment according to one embodiment.

Referring now to FIG. 1, an exemplary networked computer environment 100 in accordance with one embodiment is depicted. The networked computer environment 100 may include a computer 102 with a processor 104 and a data storage device 106 that is enabled to run an accessibility detection and resolution program 108A and a software program 114. The software program 114 may be an application program such as web program, app program, and an email program. The accessibility detection and resolution program 108A may communicate with the software program 114. The networked computer environment 100 may also include a server 112 that is enabled to run an accessibility detection and resolution program 108B and a communication network 110. The networked computer environment 100 may include a plurality of computers 102 and servers 112, only one of which is shown for illustrative brevity.

According to at least one implementation, the present embodiment may also include a database 116, which may be running on server 112. The communication network 110 may include various types of communication networks, such as a wide area network (WAN), local area network (LAN), a telecommunication network, a wireless network, a public switched network and/or a satellite network. It may be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with server computer 112 via the communications network 110. The communications network 110 may include connections, such as wire, wireless communication links, or fiber optic cables. As will be discussed with reference to FIG. 4, server computer 112 may include internal components 800a and external components 900a, respectively, and client computer 102 may include internal components 800b and external components 900b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, a set top box, a television device, or any type of computing device capable of running a program and accessing a network. According to various implementations of the present embodiment, the accessibility detection and resolution program 108A, 108B may interact with a database 116 that may be embedded in various storage devices, such as, but not limited to a mobile device 102, a networked server 112, or a cloud storage service.

According to the present embodiment, a program, such as an accessibility detection and resolution program 108A and 108B may run on the client computer 102 or on the server computer 112 via a communications network 110. The accessibility detection and resolution program 108A, 108B may generate and present accessibility resolution models based on accessibility problems associated with user interfaces and computer devices 102. Specifically, users may run an accessibility detection and resolution program 108A, 108B, on a computer 102 that may include applications and/or that may interact with devices to detect user behavior patterns on the applications and the devices, and provide accessibility resolution models based on correlations between the detected user behavior patterns, user groups and subgroups, cognitive impairments and disabilities, accessibility problems, and business loss indicators.

Figure 2:
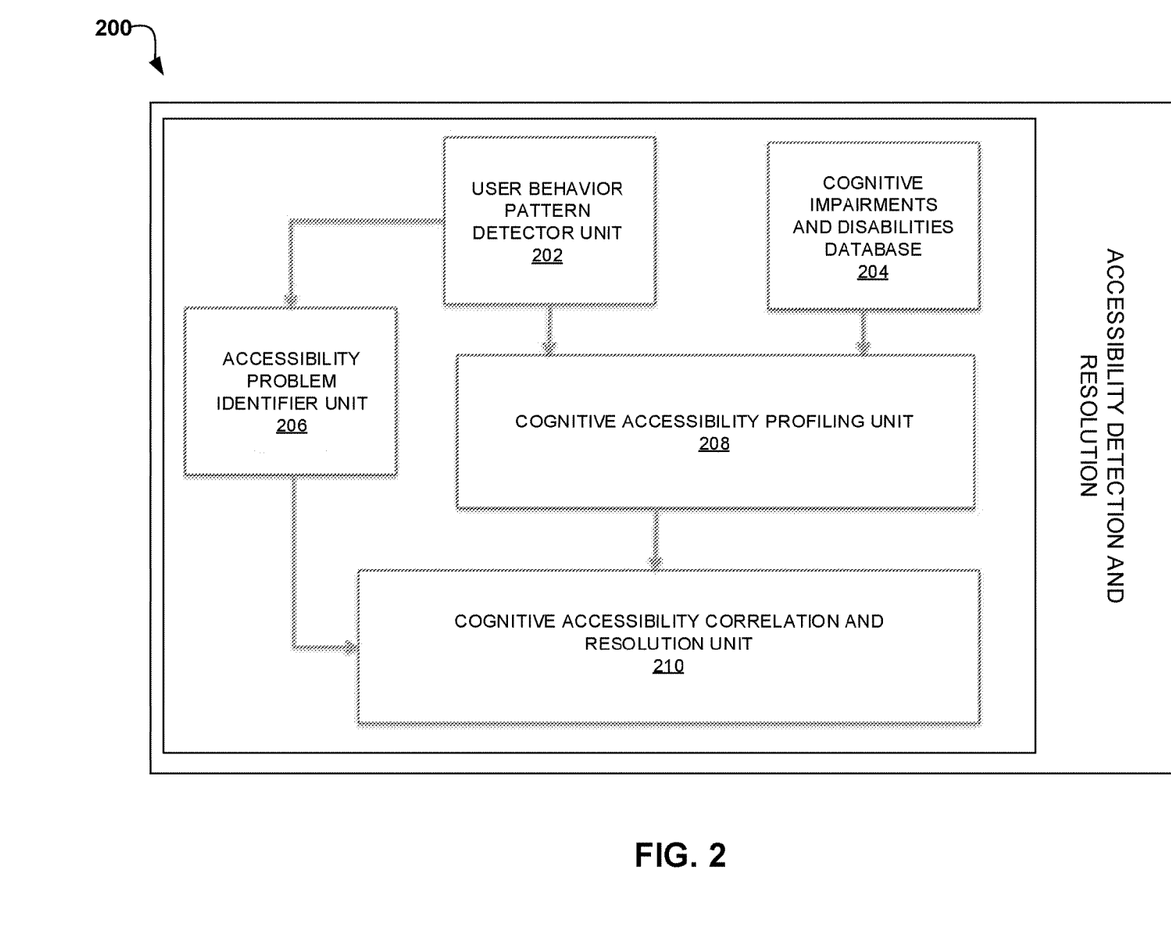
FIG. 2 is a block diagram illustrating an example of a program for generating and presenting accessibility resolution models according to one embodiment.

Referring now to FIG. 2, a block diagram 200 illustrating an example of an accessibility detection and resolution program 108A, 108B (FIG. 1) for generating and presenting accessibility resolution models is depicted. Specifically, and as previously described, the accessibility detection and resolution program 108A, 108B (FIG. 1) may generate and present accessibility resolution models based on user behavior patterns and accessibility problems associated with computer devices 102 (FIG. 1) and user interfaces. More specifically, the accessibility detection and resolution program 108A, 108B (FIG. 1) may include a user behavior pattern detector unit 202 to detect the user behavior patterns associated with the devices and applications. Additionally, the accessibility detection and resolution program 108A, 108B (FIG. 1) may include a cognitive impairments and disabilities database 204 that stores cognitive impairments and disabilities that may be associated with users based on the user behavior patterns. Furthermore, the accessibility detection and resolution program 108A, 108B (FIG. 1) may include an accessibility problem identifier unit 206 to identify accessibility problems associated with applications and devices based on the detected user behavior patterns. The accessibility detection and resolution program 108A, 108B (FIG. 1) may further include a cognitive accessibility profiling unit 208 to generate cognitive accessibility profiles based on the detected user behavior patterns, user groups and user subgroups, cognitive impairments and disabilities, and the identified accessibility problems. Thereafter, using a cognitive accessibility correlation and resolution unit 210, the accessibility detection and resolution program 108A, 108B (FIG. 1) may determine correlations between the cognitive accessibility profiles and business loss indicators to determine business loss based on the identified accessibility problems, as well as generate and present resolution models based on the determined correlation.

Figure 3:
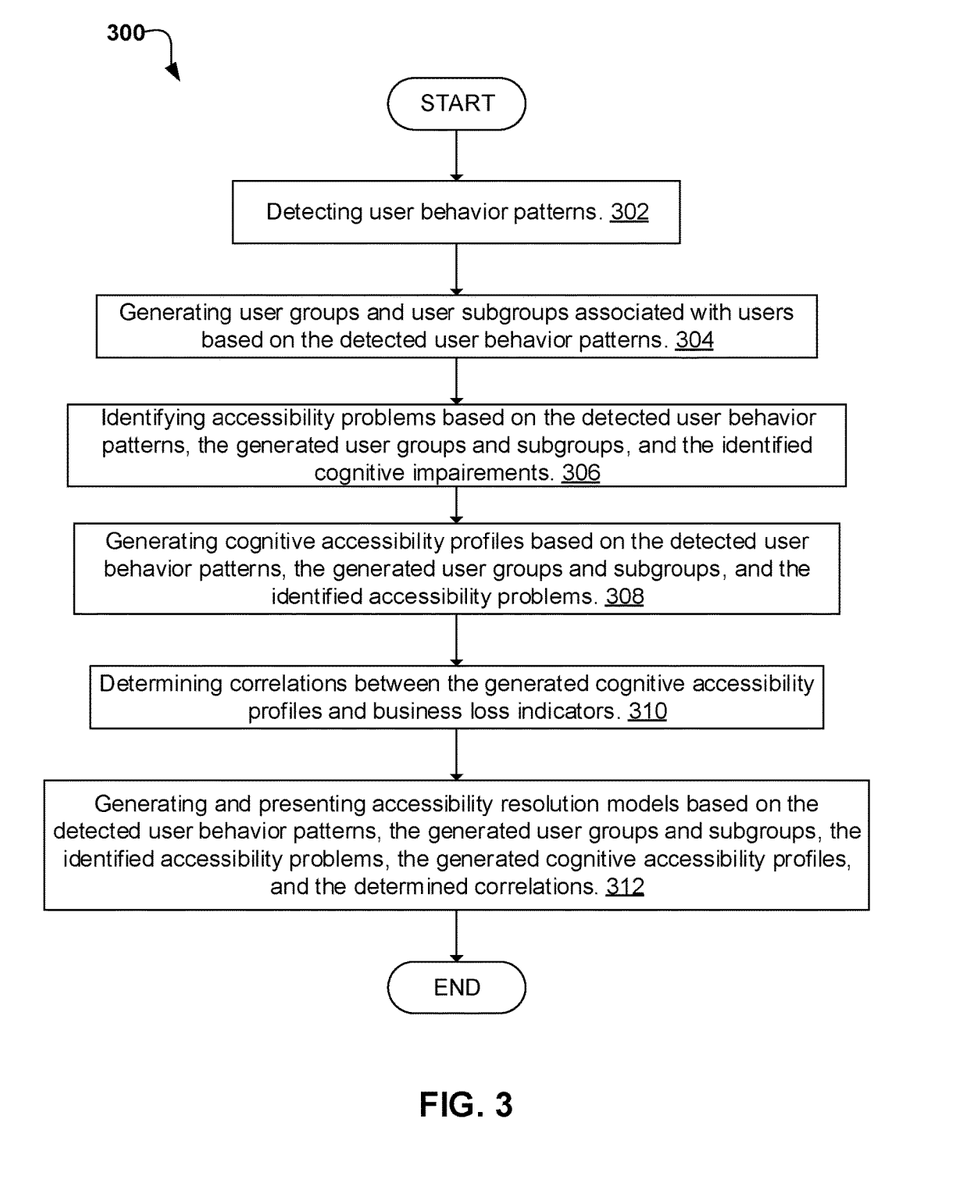
FIG. 3 is an operational flowchart illustrating the steps carried out by a program for generating and presenting accessibility resolution models according to one embodiment.

Referring now to FIG. 3, an operational flowchart 300 illustrating the steps carried out by an accessibility detection and resolution program 108A, 108B (FIG. 1) is depicted. At 302, the accessibility detection and resolution program 108A, 108B (FIG. 1) may detect user behavior patterns. Specifically, and as previously described in FIG. 2, the accessibility detection and resolution program 108A, 108B (FIG. 1) may use a user behavior pattern detector unit 202 (FIG. 2) to detect the user behavior patterns associated with such things as applications, devices, and speech/social behavior. For example, with regard to applications, the accessibility detection and resolution program 108A, 108B (FIG. 1) may detect user behavior patterns such as frequent user typos and/or word misspellings on user interfaces, failure to provide information on user interfaces such as billing address information during item checkout item, erratic navigation on user interfaces such as wrongfully and frequently clicking on links and then clicking a back button, and failing to properly use a scroll bar on user interfaces associated with websites/applications. Additionally, with regard to devices, the accessibility detection and resolution program 108A, 108B (FIG. 1) may detect user behavior patterns such as wrongfully and frequently pressing buttons on devices, such as wrongfully and frequently hitting a number key on a mobile phone device during a phone call, and wrongfully using devices associated with an internet of things (IoT) network such as different appliances and car features that exchange data with applications. Furthermore, with regard to speech/social behavior, the accessibility detection and resolution program 108A, 108B (FIG. 1) may detect user behavior patterns such as extended pauses in between speech/words during phone and/or video calls.

Then, at 304, the accessibility detection and resolution program 108A, 108B (FIG. 1) may generate user groups and user subgroups associated with users based on the detected user behavior patterns. As previously described at step 302, the accessibility detection and resolution program 108A, 108B (FIG. 1) may detect user behavior patterns associated with applications, devices, and speech, that may include frequent user typos and/or word misspellings on user interfaces, wrongfully and frequently pressing buttons on devices, and extended pauses in between speech/words during phone and/or video calls. Thereafter, the accessibility detection and resolution program 108A, 108B (FIG. 1) may generate user groups by grouping users based on the detected user behavior patterns as well as based on other factors such as age, gender, location, device information, and types of operating systems and applications. For example, the accessibility detection and resolution program 108A, 108B (FIG. 1) may generate a User Group A that includes users that make frequent typos, a User Group B that includes users that make frequent typos and have extended pauses in between speech, a User Group C that includes users that improperly use a scroll bar, a User Subgroup A1 that includes the users that make frequent typos and that are also over the age 25, a User Subgroup B1 that includes the users that make frequent typos and have extended pauses in between speech and that also use a Windows® operating system (Windows and all Windows-based trademarks and logos are trademarks or registered trademarks of Microsoft and/or its affiliates), and a User Subgroup C1 that includes the users that improperly use a scroll bar and that are also running an internet application such as Firefox® (Firefox and all Firefox-based trademarks and logos are trademarks or registered trademarks of Firefox and/or its affiliates).

Also, according to one embodiment, the accessibility detection and resolution program 108A, 108B (FIG. 1) may associate cognitive impairments and disabilities with the users based on the detected user behavior patterns and the generated user groups and user subgroups. For example, and as previously described in FIG. 2, the accessibility detection and resolution program 108A, 108B (FIG. 1) may include a cognitive impairments and disabilities database 204 (FIG. 2) to store user behavior patterns and cognitive impairments that are associated with the stored user behavior patterns. Specifically, the accessibility detection and resolution program 108A, 108B (FIG. 1) may include a cognitive impairments and disabilities database 204 (FIG. 2) that stores cognitive impairments such as mild cognitive impairments (MCIs), attention deficit disorder (ADD), age appropriate forgetfulness, intellectual disabilities, diminished visual memory, dementia, learning disabilities such as dyslexia, as well as cognitive impairments based on user circumstances such as distraction, fatigue, deterioration in health, stress, and trauma that may be based on user location and/or work-life balance.

Therefore, based on the detected user behavior patterns, the accessibility detection and resolution program 108A, 108B (FIG. 1) may identify the cognitive impairments and disabilities that may be associated with the users of the generated user groups and subgroups. Specifically, for example, the accessibility detection and resolution program 108A, 108B (FIG. 1) may detect user behavior patterns such as users making frequent typos on a user interface and generate a User Group A that includes the users that make frequent typos. Thereafter, the accessibility detection and resolution program 108A, 108B (FIG. 1) may identify cognitive impairments and disabilities that may be associated with the users that make frequent typos, as well as determine percentage levels for the identified cognitive impairments and disabilities, such as determining that users that make frequent typos may have a 50% chance of age appropriate forgetfulness, and a 20% chance of dyslexia if the users are born in country A, or a 30% chance of dyslexia if the users are born in country B.

Next, at 306, the accessibility detection and resolution program 108A, 108B (FIG. 1) may identify accessibility problems associated with applications and devices based on the detected user behavior patterns, the generated user groups and user subgroups and the identified cognitive impairments. Specifically, and as previously described in FIG. 2, the accessibility detection and resolution program 108A, 108B (FIG. 1) may use an accessibility problem identifier unit 206 (FIG. 2) to identify accessibility problems associated with applications and devices based on the detected user behavior patterns. For example, the accessibility detection and resolution program 108A, 108B (FIG. 1) may detect a user behavior pattern such as a user frequently having typos when entering information on a user interface of an online shopping website and/or application during an item purchase at checkout. Thereafter, the accessibility detection and resolution program 108A, 108B (FIG. 1) may generate a User Group A that includes the users that make frequent typos. Furthermore, the accessibility detection and resolution program 108A, 108B (FIG. 1) may identify accessibility problems associated with the User Group A such as determining that the users in User Group A may typically get stuck on a certain page of a website/application, may abandon transactions based on the frequent typos, and may find it difficult to navigate an application or use certain features. As such, the accessibility detection and resolution program 108A, 108B (FIG. 1) may identify accessibility problems associated with the pages that users in User Group A may get stuck on, accessibility problems associated with checking out items, and accessibility problems associated with the features that the users in User Group A find difficult to use.

Then, at 308, the accessibility detection and resolution program 108A, 108B (FIG. 1) may generate cognitive accessibility profiles based on the detected user behavior patterns, the generated user groups and user subgroups, and the identified accessibility problems. Specifically, and as previously described in FIG. 2, the accessibility detection and resolution program 108A, 108B (FIG. 1) may use a cognitive accessibility profiling unit 208 (FIG. 2) to generate the cognitive accessibility profiles that may include profiles of users based on the detected user behavior patterns, the generated user groups and user subgroups, and the identified accessibility problems associated with the users. For example, and as previously described at step 302, the accessibility detection and resolution program 108A, 108B (FIG. 1) may detect user behavior patterns such as frequent typos made by users as well as omissions of information when checking out items. Furthermore, based on the detected user behavior pattern, the accessibility detection and resolution program 108A, 108B (FIG. 1) may generate user groups and user subgroups such as User Group A and User Subgroup A1 as previously described at step 304. Additionally, according to one embodiment, and as previously described, the accessibility detection and resolution program 108A, 108B (FIG. 1) may associate cognitive impairments and disabilities with the users in User Group A, such as age appropriate forgetfulness, ADD and dyslexia. Also, and as previously described at step 306, the accessibility detection and resolution program 108A, 108B (FIG. 1) may identify accessibility problems associated with the pages that users in User Group A may get stuck on, accessibility problems associated with checking out items, and accessibility problems associated with the features that the users in User Group A find difficult to use. Therefore, the accessibility detection and resolution program 108A, 108B (FIG. 1) may generate a cognitive accessibility profile for users in User Group A that identifies the users as individuals that make frequent typos, that may suffer from dyslexia, ADD, and age appropriate forgetfulness, that are likely to cancel item transactions based on the frequent typos, and that accessibility problems associated with checking out items and certain features of applications may be identified based on the users in User Group A.

Next, at 310, based on the generated cognitive accessibility profiles, the accessibility detection and resolution program 108A, 108B (FIG. 1) may determine correlations between the generated cognitive accessibility profiles and business loss indicators. Specifically, and as previously described in FIG. 2, the accessibility detection and resolution program 108A, 108B (FIG. 1) may use a cognitive accessibility correlation and resolution unit 210 (FIG. 2) to determine the business loss indicators, such as loss of sales and loss of productivity, based on the businesses associated with the user interfaces and/or computer devices 102 (FIG. 1) affected by the accessibility problems, and correlate the determined business loss indicators with the generated cognitive accessibility profiles. Furthermore, the accessibility detection and resolution program 108A, 108B (FIG. 1) may correlate the determined business loss indicators with the generated cognitive accessibility profiles by determining causal connections between the detected user behavior patterns, the determined cognitive impairments, the identified accessibility problems, the generated cognitive accessibility profiles, and the business loss indicators.

For example, and as previously described at step 308, based on the detected user behavior patterns, the generated user groups and user subgroups, and the identified accessibility problems, the accessibility detection and resolution program 108A, 108B (FIG. 1) may generate a cognitive accessibility profile that identifies the users in a User Group A as individuals that make frequent typos, that may suffer from dyslexia, ADD, and age appropriate forgetfulness, that are likely to cancel item transactions based on the frequent typos, and that accessibility problems associated with checking out items and certain features of applications may be identified based on the users in User Group A. Also, for example, the accessibility detection and resolution program 108A, 108B (FIG. 1) may generate a cognitive accessibility profile that identifies users in a User Group D that erratically navigate user interfaces, such as wrongfully and frequently clicking on links and then clicking a back button on websites/applications, as users that may suffer from ADD, dementia, diminished visual memory, and stress, as well as users that may likely exit user interfaces associated with websites/applications. Therefore, based on the generated cognitive accessibility profiles, the accessibility detection and resolution program 108A, 108B (FIG. 1) may determine and correlate business loss indicators, such as determining and correlating a business loss that indicates that a sales loss of $25,000 may be due to the generated cognitive accessibility profile associated with the users in the User Group A, and indicates that a sales loss of $10,000 may be due to the generated cognitive accessibility profile associated with the users in the User Group D.

Then, at 312, the accessibility detection and resolution program 108A, 108B (FIG. 1) may generate and present accessibility resolution models based on the detected user behavior patterns, the generated user groups and user subgroups, the identified accessibility problems, the generated cognitive accessibility profiles, and the determined correlations between the cognitive accessibility profiles and business loss indicators. Specifically, and as previously described in FIG. 2, the accessibility detection and resolution program 108A, 108B (FIG. 1) may use the cognitive accessibility correlation and resolution unit 210 (FIG. 2) to generate and present accessibility resolution models that may include diagrams and may provide resolutions to the accessibility problems associated with user interfaces and computer devices 102 (FIG. 1). More specifically, the accessibility detection and resolution program 108A, 108B (FIG. 1) may generate and present accessibility resolution models that may include diagrams such as heat maps, graphs, charts, and Venn diagrams that present and provide resolutions to the determined correlations between the cognitive accessibility profiles and the business loss indicators.

For example, and as previously described at step 310, based on the detected user behavior patterns, the determined cognitive impairments, the identified accessibility problems, and the generated cognitive accessibility profiles, the accessibility detection and resolution program 108A, 108B (FIG. 1) may determine correlations between the generated cognitive accessibility profiles and the determined business loss indicators, such as by determining that a sales loss of $25,000 may be due to the generated cognitive accessibility profile associated with the users in the User Group A, and that a sales loss of $10,000 may be due to the generated cognitive accessibility profile associated with the users in the User Group D. Therefore, for example, the accessibility detection and resolution program 108A, 108B (FIG. 1) may generate and present accessibility resolution models that may include diagrams that present the determined correlations between the cognitive accessibility profiles and the business loss indicators based on the User Group A and the User Group D, such as by presenting a diagram of the different detected user behavior patterns associated with the cognitive accessibility profiles and the correlation to the accessibility problems, presenting a diagram of the determined cognitive impairments associated with the cognitive accessibility profiles and the correlation to the accessibility problems, presenting a diagram of the cognitive accessibility profiles and the correlation to the business loss indicators, and presenting the user subgroups associated with the user groups and the user subgroup effect on the business loss indicators. Furthermore, according to one embodiment, the accessibility detection and resolution program 108A, 108B (FIG. 1) may present a diagram showing suggested design modifications to the application and devices based on the correlations between the cognitive accessibility profiles and the business loss indicators.

It may be appreciated that FIGS. 2 and 3 provide only illustrations of one implementation and do not imply any limitations with regard to how different embodiments may be implemented. Many modifications to the depicted environments may be made based on design and implementation requirements. For example, at step 302 in FIG. 3, the accessibility detection and resolution program 108A, 108B (FIG. 1) may collect user profile data based on the users associated with the detected user behavior patterns and store the user profile data on a database such as database 116 (FIG. 1). For example, the accessibility detection and resolution program 108A, 108B (FIG. 1) may collect user profile data based on information provided by the user such as a created profile associated with a website/application that may include user name, age, and location data, as well as based on IP addresses.

Furthermore, the accessibility detection and resolution program 108A, 108B (FIG. 1) may generate and present accessibility resolution models based on determined correlations between cognitive accessibility profiles associated with employees of businesses. Specifically, for example, the accessibility detection and resolution program 108A, 108B (FIG. 1) may detect user behavior patterns associated with employees of a business such as frequently not responding to emails and frequent typos on certain tasks, may generate user groups and user subgroups based on the detected user behavior patterns, may determine cognitive impairments associated with the employees such as ADD and diminished memory for the employee, may identify accessibility problems such as failure to complete tasks, and may determine business loss indicators that may indicate loss of acquisition of an employee and/or loss of productivity from employees. Thereafter, the accessibility detection and resolution program 108A, 108B (FIG. 1) may generate and present accessibility resolution models based on determined correlations between cognitive accessibility profiles associated with the employees to resolve the accessibility problem of failed tasks.

Figure 4:
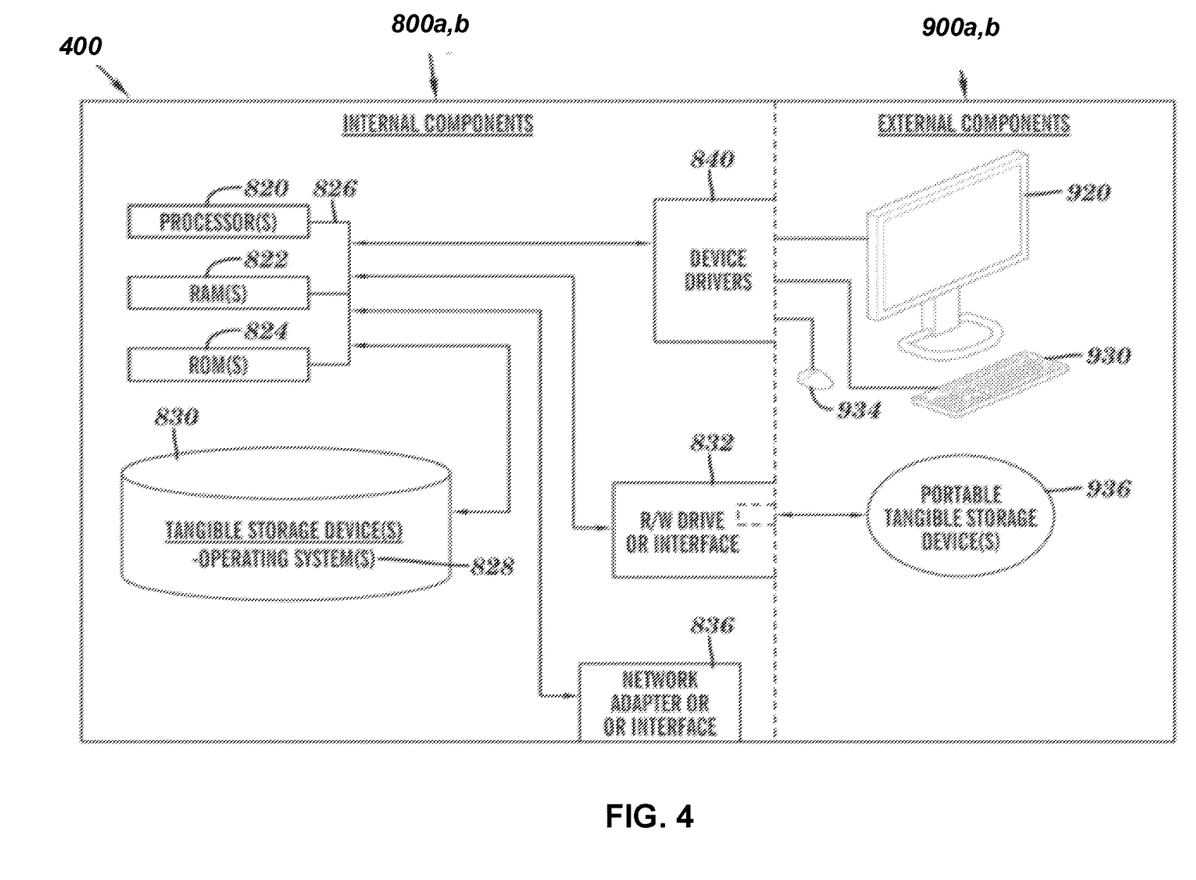
FIG. 4 is a block diagram of the system architecture of a program for generating and presenting accessibility resolution models according to one embodiment.

FIG. 4 is a block diagram 400 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may be represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 (FIG. 1) and network server 112 (FIG. 1) include respective sets of internal components 800a, b and external components 900a, b illustrated in FIG. 4. Each of the sets of internal components 800a, b includes one or more processors 820, one or more computer-readable RAMs 822, and one or more computer-readable ROMs 824 on one or more buses 826, and one or more operating systems 828 and one or more computer-readable tangible storage devices 830. The one or more operating systems 828, the software program 114 (FIG. 1) and the accessibility detection and resolution program 108A (FIG. 1) in client computer 102 (FIG. 1), and the accessibility detection and resolution program 108B (FIG. 1) in network server computer 112 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory, or any other computer-readable tangible storage device that can store a computer program and digital information.

Each set of internal components 800a, b, also includes a R/W drive or interface 832 to read from and write to one or more portable computer-readable tangible storage devices 936 such as a CD-ROM, DVD, memory stick, magnetic tape, magnetic disk, optical disk or semiconductor storage device. A software program, such as an accessibility detection and resolution program 108A and 108B (FIG. 1), can be stored on one or more of the respective portable computer-readable tangible storage devices 936, read via the respective R/W drive or interface 832, and loaded into the respective hard drive 830.

Each set of internal components 800a, b also includes network adapters or interfaces 836 such as a TCP/IP adapter cards, wireless Wi-Fi interface cards, or 3G or 4G wireless interface cards or other wired or wireless communication links. The accessibility detection and resolution program 108A (FIG. 1) and software program 114 (FIG. 1) in client computer 102 (FIG. 1), and the accessibility detection and resolution program 108B (FIG. 1) in network server 112 (FIG. 1) can be downloaded to client computer 102 (FIG. 1) from an external computer via a network (for example, the Internet, a local area network or other, wide area network) and respective network adapters or interfaces 836. From the network adapters or interfaces 836, the accessibility detection and resolution program 108A (FIG. 1) and software program 114 (FIG. 1) in client computer 102 (FIG. 1) and the accessibility detection and resolution program 108B (FIG. 1) in network server computer 112 (FIG. 1) are loaded into the respective hard drive 830. The network may comprise copper wires, optical fibers, wireless transmission, routers, firewalls, switches, gateway computers, and/or edge servers.

Each of the sets of external components 900a, b can include a computer display monitor 920, a keyboard 930, and a computer mouse 934. External components 900a, b can also include touch screens, virtual keyboards, touch pads, pointing devices, and other human interface devices. Each of the sets of internal components 800a, b also includes device drivers 840 to interface to computer display monitor 920, keyboard 930, and computer mouse 934. The device drivers 840, R/W drive or interface 832, and network adapter or interface 836 comprise hardware and software (stored in storage device 830 and/or ROM 824).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
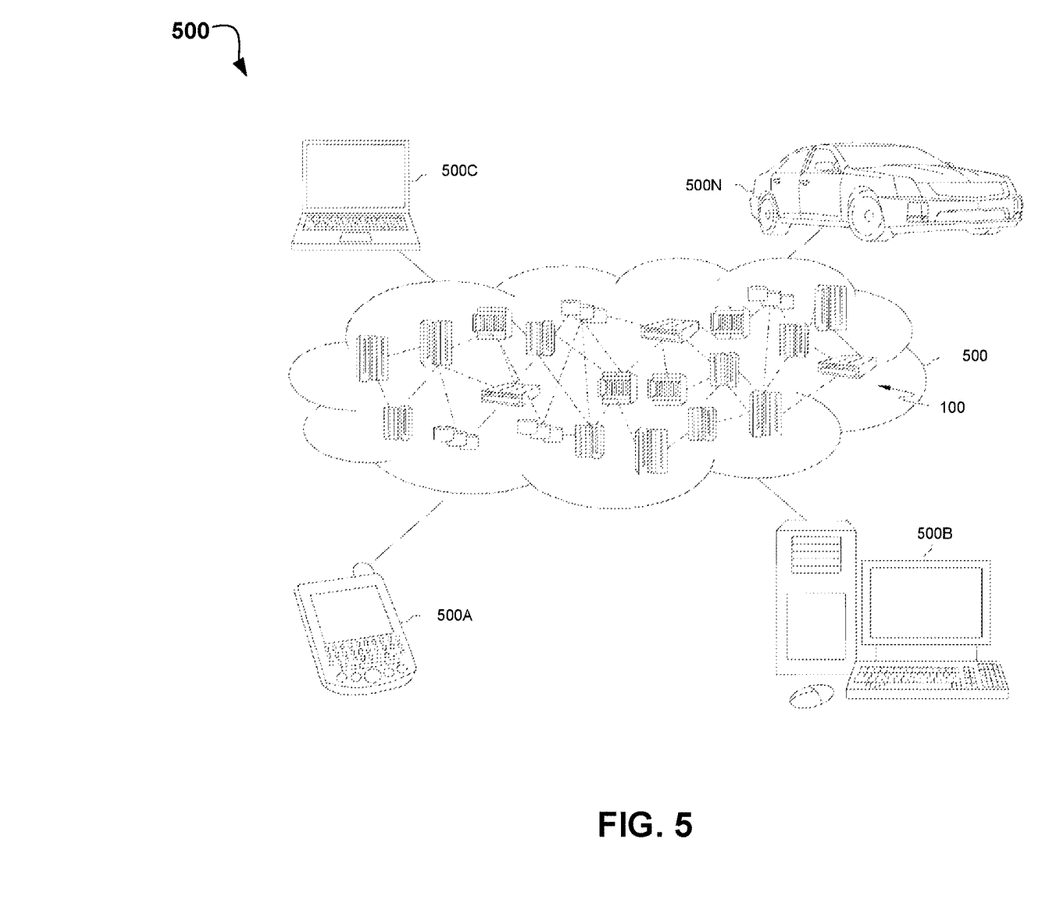
FIG. 5 is a block diagram of an illustrative cloud computing environment including the computer system depicted in FIG. 1, in accordance with an embodiment of the present disclosure.

Referring now to FIG. 5, illustrative cloud computing environment 500 is depicted. As shown, cloud computing environment 500 comprises one or more cloud computing nodes 100 with which local computing devices used by cloud consumers, such as, for example, personal digital assistant (PDA) or cellular telephone 500A, desktop computer 500B, laptop computer 500C, and/or automobile computer system 500N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 500A-N shown in FIG. 5 are intended to be illustrative only and that computing nodes 100 and cloud computing environment 500 can communicate with any type of computerized device over any type of network and/or network addressable connection (e.g., using a web browser).

Figure 6:
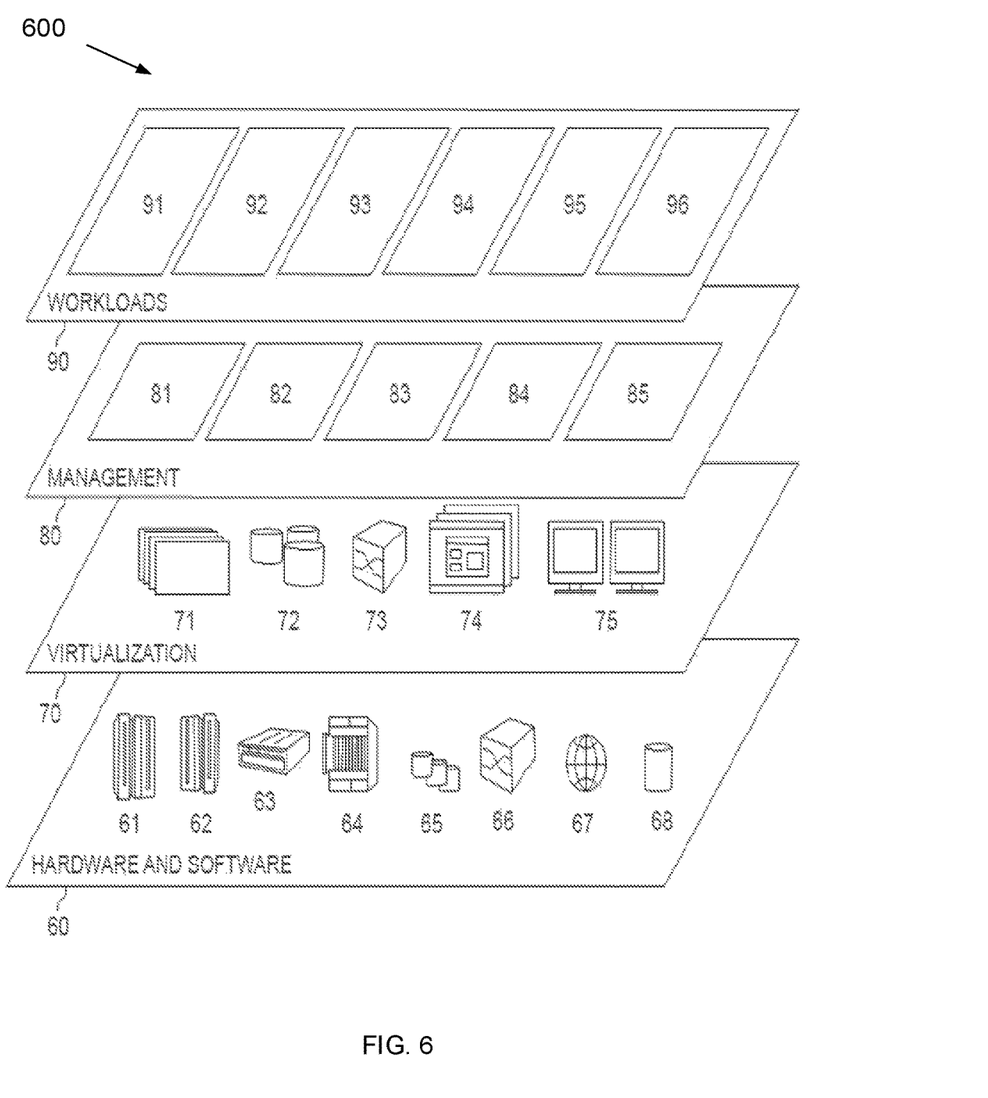
FIG. 6 is a block diagram of functional layers of the illustrative cloud computing environment of FIG. 5, in accordance with an embodiment of the present disclosure.

Referring now to FIG. 6, a set of functional abstraction layers 600 provided by cloud computing environment 500 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and accessibility detection and resolution 96. An accessibility detection and resolution program 108A, 108B (FIG. 1) may be offered "as a service in the cloud" (i.e., Software as a Service (SaaS)) for applications running on mobile devices 102 (FIG. 1) and may generate and present accessibility resolution models to accessibility problems associated with users based on user behavior patterns.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for generating and presenting a plurality of accessibility resolution models based on a plurality of user behavior patterns, the method comprising:
   detecting the plurality of user behavior patterns associated with one or more users;
   generating a plurality of user groups and a plurality of user subgroups based on the one or more users and the plurality of user behavior patterns;
   identifying a plurality of accessibility problems based on the detected plurality of user behavior patterns, the generated plurality of user groups, and the generated plurality of user subgroups;
   generating a plurality of accessibility profiles based on the detected plurality of user behavior patterns, the generated plurality of user groups, the generated plurality of user subgroups, and the identified plurality of accessibility problems;
   determining at least one correlation between the generated plurality of accessibility profiles and at least one business loss indicator; and
   generating and presenting the plurality of accessibility resolution models for the identified plurality of accessibility problems based on the detected plurality of user behavior patterns, the generated plurality of user groups, the generated plurality of user subgroups, and the determined at least one correlation between the generated plurality of accessibility profiles and the at least one business loss indicator.

2. The method of claim 1, wherein the plurality of user behavior patterns are selected from the group consisting of a plurality of improper application uses of at least one feature associated with at least one application, a plurality of improper device uses associated with at least one device, and a plurality of speech problems.

3. The method of claim 1, wherein generating the plurality of user groups and the plurality of user subgroups further comprises:
   identifying and associating a plurality of impairments and disabilities with the one or more users, wherein the plurality of impairments and disabilities are selected from the group consisting of a mild cognitive impairment (MCI), an attention deficit disorder (ADD), an age appropriate forgetfulness, an intellectual disability, a diminished visual memory, and a learning disability.

4. The method of claim 1, wherein the identified plurality of accessibility problems are selected from the group consisting of at least one application problem associated with one or more applications and at least one device problem associated with one or more devices.

5. The method of claim 1, wherein the at least one business loss indicator is selected from the group consisting of a loss of sales and a loss of productivity.

6. The method of claim 3, wherein determining at least one correlation between the generated plurality of accessibility profiles and the at least one business loss indicator further comprises:
   determining a plurality of causal connections between the detected plurality of user behavior patterns, the identified and associated plurality of impairments and disabilities, the identified plurality of accessibility problems, the generated plurality of accessibility profiles, and the at least one business loss indicator.

7. The method of claim 1, wherein generating and presenting the plurality of accessibility resolution models further comprises:
   generating and presenting at least one diagram and at least one resolution to the identified plurality of accessibility problems.

8. A computer system for generating and presenting a plurality of accessibility resolution models based on a plurality of user behavior patterns, comprising:
   one or more processors, one or more computer-readable memories, one or more computer-readable tangible storage devices, and program instructions stored on at least one of the one or more storage devices for execution by at least one of the one or more processors via at least one of the one or more memories, wherein the computer system is capable of performing a method comprising:
   detecting the plurality of user behavior patterns associated with one or more users;
   generating a plurality of user groups and a plurality of user subgroups based on the one or more users and the plurality of user behavior patterns;
   identifying a plurality of accessibility problems based on the detected plurality of user behavior patterns, the generated plurality of user groups, and the generated plurality of user subgroups;
   generating a plurality of accessibility profiles based on the detected plurality of user behavior patterns, the generated plurality of user groups, the generated plurality of user subgroups, and the identified plurality of accessibility problems;
   determining at least one correlation between the generated plurality of accessibility profiles and at least one business loss indicator; and
   generating and presenting the plurality of accessibility resolution models for the identified plurality of accessibility problems based on the detected plurality of user behavior patterns, the generated plurality of user groups, the generated plurality of user subgroups, and the determined at least one correlation between the generated plurality of accessibility profiles and the at least one business loss indicator.

9. The computer system of claim 8, wherein the plurality of user behavior patterns are selected from the group consisting of a plurality of improper application uses of at least one feature associated with at least one application, a plurality of improper device uses associated with at least one device, and a plurality of speech problems.

10. The computer system of claim 8, wherein generating the plurality of user groups and the plurality of user subgroups further comprises:
identifying and associating a plurality of impairments and disabilities with the one or more users, wherein the plurality of impairments and disabilities are selected from the group consisting of a mild cognitive impairment (MCI), an attention deficit disorder (ADD), an age appropriate forgetfulness, an intellectual disability, a diminished visual memory, and a learning disability.

11. The computer system of claim 8, wherein the identified plurality of accessibility problems are selected from the group consisting of at least one application problem associated with one or more applications and at least one device problem associated with one or more devices.

12. The computer system of claim 8, wherein the at least one business loss indicator is selected from the group consisting of a loss of sales and a loss of productivity.

13. The computer system of claim 10, wherein determining at least one correlation between the generated plurality of accessibility profiles and the at least one business loss indicator further comprises:
determining a plurality of causal connections between the detected plurality of user behavior patterns, the identified and associated plurality of impairments and disabilities, the identified plurality of accessibility problems, the generated plurality of accessibility profiles, and the at least one business loss indicator.

14. The computer system of claim 8, wherein generating and presenting the plurality of accessibility resolution models further comprises:
generating and presenting at least one diagram and at least one resolution to the identified plurality of accessibility problems.

15. A computer program product for generating and presenting a plurality of accessibility resolution models based on a plurality of user behavior patterns, comprising:
one or more computer-readable storage devices and program instructions stored on at least one of the one or more tangible storage devices, the program instructions executable by a processor, the program instructions comprising:
program instructions to detect the plurality of user behavior patterns associated with one or more users;
program instructions to generate a plurality of user groups and a plurality of user subgroups based on the one or more users and the plurality of user behavior patterns;
program instructions to identify a plurality of accessibility problems based on the detected plurality of user behavior patterns, the generated plurality of user groups, and the generated plurality of user subgroups;
program instructions to generate a plurality of accessibility profiles based on the detected plurality of user behavior patterns, the generated plurality of user groups, the generated plurality of user subgroups, and the identified plurality of accessibility problems;
program instructions to determine at least one correlation between the generated plurality of accessibility profiles and at least one business loss indicator; and
program instructions to generate and present the plurality of accessibility resolution models for the identified plurality of accessibility problems based on the detected plurality of user behavior patterns, the generated plurality of user groups, the generated plurality of user subgroups, and the determined at least one correlation between the generated plurality of accessibility profiles and the at least one business loss indicator.

16. The computer program product of claim 15, wherein the plurality of user behavior patterns are selected from the group consisting of a plurality of improper application uses of at least one feature associated with at least one application, a plurality of improper device uses associated with at least one device, and a plurality of speech problems.

17. The computer program product of claim 15, wherein the program instructions to generate the plurality of user groups and the plurality of user subgroups further comprises:
program instructions to identify and associate a plurality of impairments and disabilities with the one or more users, wherein the plurality of impairments and disabilities are selected from the group consisting of a mild cognitive impairment (MCI), an attention deficit disorder (ADD), an age appropriate forgetfulness, an intellectual disability, a diminished visual memory, and a learning disability.

18. The computer program product of claim 15, wherein the at least one business loss indicator is selected from the group consisting of a loss of sales and a loss of productivity.

19. The computer program product of claim 17, wherein the program instructions to determine at least one correlation between the generated plurality of accessibility profiles and the at least one business loss indicator further comprises:
program instructions to determine a plurality of causal connections between the detected plurality of user behavior patterns, the identified and associated plurality of impairments and disabilities, the identified plurality of accessibility problems, the generated plurality of accessibility profiles, and the at least one business loss indicator.

20. The computer program product of claim 15, wherein the program instructions to generate and present the plurality of accessibility resolution models further comprises:
program instructions to generate and present at least one diagram and at least one resolution to the identified plurality of accessibility problems.

* * * * *